United States Patent
Cucumel et al.

(10) Patent No.: US 10,806,693 B2
(45) Date of Patent: Oct. 20, 2020

(54) **METHOD FOR INCREASING LIPOLYSIS USING A COMPOSITION COMPRISING BIOACTIVE *NELUMBO NUCIFERA* (LOTUS) EXTRACT**

(71) Applicant: ISP Investments LLC, Wilmington, DE (US)

(72) Inventors: Karine Cucumel, Opio (FR); Isabelle Imbert, Cannes (FR); Nouha Domloge, Opio (FR); Olga Dueva-Koganov, White Plains, NY (US); Michael Koganov, White Plains, NY (US)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 16/325,536

(22) PCT Filed: Sep. 6, 2017

(86) PCT No.: PCT/US2017/050264
§ 371 (c)(1),
(2) Date: Feb. 14, 2019

(87) PCT Pub. No.: WO2018/048892
PCT Pub. Date: Mar. 15, 2018

(65) Prior Publication Data
US 2019/0201320 A1    Jul. 4, 2019

Related U.S. Application Data

(60) Provisional application No. 62/384,359, filed on Sep. 7, 2016.

(51) Int. Cl.
| | | |
|---|---|---|
| *A61K 36/62* | (2006.01) | |
| *A61K 8/9789* | (2017.01) | |
| *A61Q 19/06* | (2006.01) | |
| *A61K 8/97* | (2017.01) | |
| *A61Q 90/00* | (2009.01) | |
| *A61Q 19/00* | (2006.01) | |

(52) U.S. Cl.
CPC ............ *A61K 8/9789* (2017.08); *A61K 8/97* (2013.01); *A61Q 19/00* (2013.01); *A61Q 19/06* (2013.01); *A61Q 90/00* (2013.01)

(58) Field of Classification Search
None
See application file for complete search history.

(56) References Cited

U.S. PATENT DOCUMENTS

| | | | |
|---|---|---|---|
| 6,468,564 B1 * | 10/2002 | Riley | A61K 8/97 424/725 |
| 2003/0007988 A1 * | 1/2003 | Courtin | A61K 8/645 424/401 |
| 2009/0148544 A1 * | 6/2009 | Archambault | A61K 8/606 424/725 |
| 2011/0212190 A1 * | 9/2011 | Koganov | A61K 8/9789 424/711 |
| 2013/0028996 A1 * | 1/2013 | Koganov | A61Q 19/08 424/757 |
| 2016/0263013 A1 * | 9/2016 | Brownell | A61K 8/97 |
| 2017/0340556 A1 * | 11/2017 | Koganov | A61K 36/48 |
| 2019/0282491 A1 * | 9/2019 | Dueva-Koganov | A61K 8/9789 |

FOREIGN PATENT DOCUMENTS

| | | | |
|---|---|---|---|
| JP | 2004 224789 | * | 8/2004 |
| WO | WO 2012/072670 A2 | * | 6/2012 |
| WO | WO2012/072670 A2 | | 6/2012 |

OTHER PUBLICATIONS

Lenaers, C. et al. Triple Target for a High Anti-Cellulite Action. Fragrance J 36(8)88-93, 2008. (Year: 2008).*
International Search Report of PCT Application No. PCT/US2017/050264 published on Mar. 15, 2018.
Ono Y et al: 11Anti-obesity effect of *Nelumbo nucifera* leaves extract in mice and rats 11, Medicinal & Aromatic Plants Abstracts, Scientific Publishers, Scientific Publishers, New Delhi—India,vol. 28, No. 6, Dec. 1, 2006 (Dec. 1, 2006), XP018019885, ISSN: 0250-4367.

* cited by examiner

*Primary Examiner* — Ralph J Gitomer
(74) *Attorney, Agent, or Firm* — William J. Davis; Nathalie Tietcheu

(57) ABSTRACT

The present invention is related to a cosmetic method for promoting lipolysis, slimming, draining, smooth skin surface, reducing the volume of localized fat deposits, the method including applying a topical composition comprising a *Nelumbo nucifera* (Lotus) Extract.

4 Claims, 1 Drawing Sheet

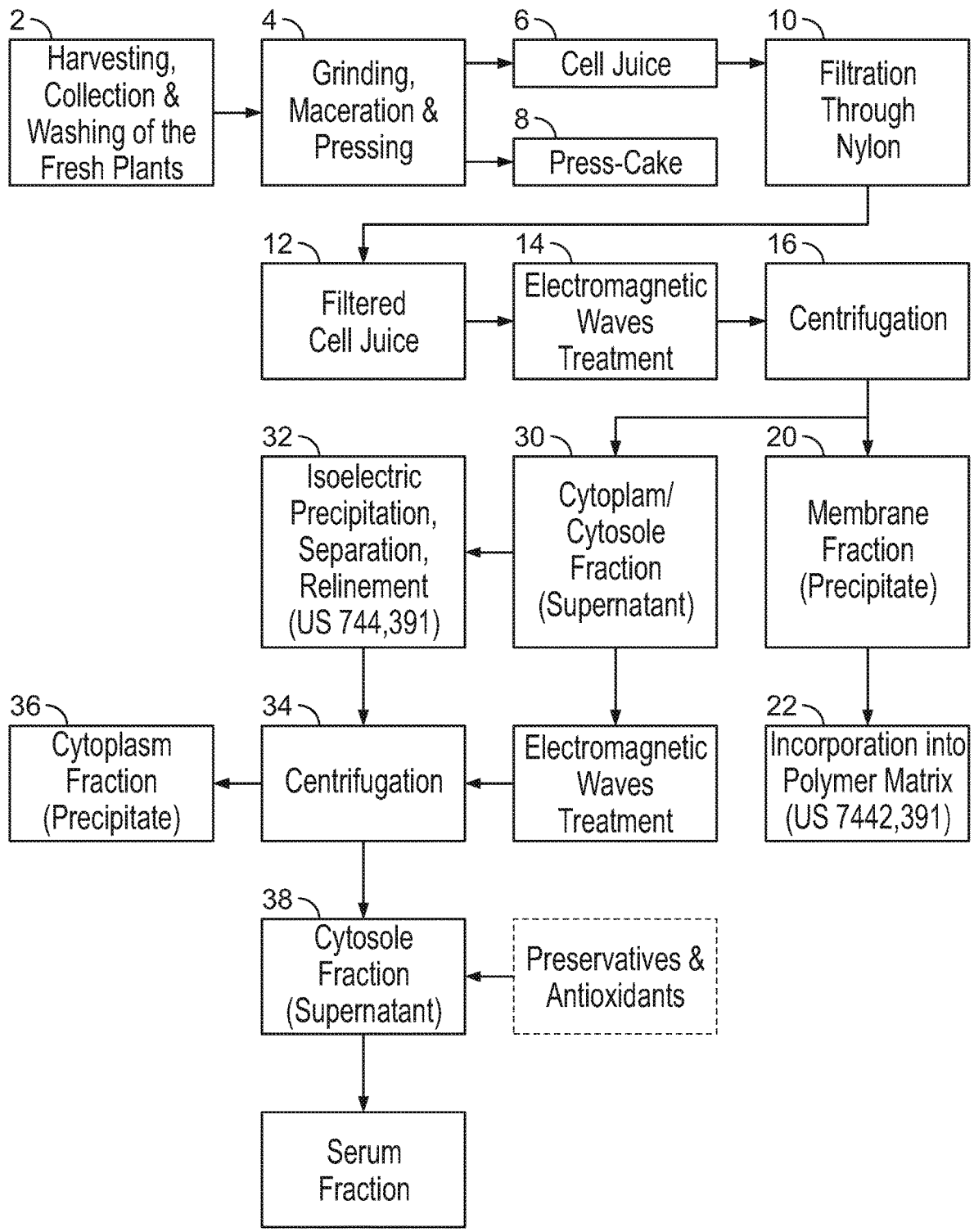

METHOD FOR INCREASING LIPOLYSIS USING A COMPOSITION COMPRISING BIOACTIVE *NELUMBO NUCIFERA* (LOTUS) EXTRACT

FIELD OF THE INVENTION

The present invention relates to the field of cosmetics and more specifically the field of cosmetic slimming methods. It relates to the cosmetic use of a bioactive ingredient obtained from *Nelumbo nucifera* Gaertn. (Lotus) fresh (living) plant as slimming and draining cosmetic agent.

The invention also relates to a method of cosmetic care including the topical application, on at least a portion of the skin of the body or the face, of a *Nelumbo nucifera* (Lotus) extract in a composition containing a physiologically acceptable medium, in order to obtain a slimming effect, and more specifically to reduce localized excess body fat.

BACKGROUND

The subcutaneous adipose tissue is located at the hypodermis. It is a type of connective tissue where adipocytes are predominant, organized in lobes around 5 mm in diameter, separated by fine connective bridges. Each adipocyte contains a voluminous lipid vacuole containing essentially triglycerides and having a diameter that may range from 40 to 120.mu.m.

Adipose tissue may be considered to be a dynamic reservoir, constantly being renewed, balancing the dietary intake with the energy requirements of the body. Thus, adipocytes ensure the synthesis, accumulation and release of lipids.

Lipid synthesis, or lipogenesis, originates with triglycerides of dietary origin and glucose. Conversely, the triglycerides stored in the adipocytes may be hydrolyzed, during lipolysis, to release fatty acids, glycerol and glycerol mono- and diesters.

The non-esterified fatty acids thus released may circulate in the blood and then be available for the energy requirements of other cells of the body, or be quickly reused by the adipocyte so as to generate, again, triglycerides by lipogenesis.

If a sustained imbalance occurs in the body promoting lipogenesis, the quantity of lipids stored in the adipocytes increases, leading to hyperplasia of the mass of body fat and more specifically to the appearance of localized excess body fat. In fact, in human adults, under the effect of sex hormones, the adipose tissue is distributed differently according to sex and forms the silhouette. Adipose tissue accumulates in the chest, on the hips, the buttocks and the thighs in women, and on the nape and shoulders in men. In addition, localized excess body fat is often associated with modifications in the skin, which develops a dimpled or "orange-peel" appearance. This localized excess body fat is currently considered to be unattractive. The invention is intended for people in good health that may want to improve the appearance of their skin and silhouette, reduce localized excess body fat using cosmetic methods.

It has been proposed that the anatomical structure of subcutaneous adipose tissue is the major cause of cellulite. The histological studies of subcutaneous tissues from men and women suggest that the fat lobules are larger and more vertical in women than men. As a result, these larger, less restricted lobules can express outward against the dermis causing the bumps and dimples characteristic of cellulite. The femoral subcutaneous fat deposits in women also tend to be more lipogenic and less lipolytic than abdominal subcutaneous or visceral fat due to the difference in the distribution of alpha and beta adrenergic receptors on adipocytes in these different regions. Increased lipolysis or fat reduction of these selected subcutaneous adipose sites may lead to a reduction or the prevention of cellulite.

Among the methods for stimulating lipolysis, the most commonly known and used is that which consists in inhibiting the phosphodiesterase in order to prevent or at least limit the rate of degradation of cyclic AMP. In effect, the phosphodiesterase destroys cyclic AMP by transforming it into 5' AMP so that it cannot function as a lipolysis activator. Topical application for the treatment of cellulite of agents capable of distributing or reducing local fat accumulation by lipolytic action thereby improving the aesthetic appearance of the skin has been used. Among the common agents for treatment of cellulite as slimming agents are xanthine analogs such as caffeine or theophylline. These agents block the antilipolytic action of adenosine, a potent endogenous inhibitor of lipolysis.

Numerous active agents having an action on lipolysis or lipogenesis, intended for slimming effect, have thus been identified. Among them, the following may be cited: Xanthine bases (xanthine derivatives), such as theophylline, caffeine, theobromine (described in patents FR 2 609 395, FR 2 674 01), used for their action promoting the lipolytic activity of fat cells. Synthetic peptides, such as the peptide of sequence Arg-Gly-Ser-NH2 (described in patent FR 2 858 769), or the peptide of sequence Pro-Leu-Asp-Thr-Ala-Lys-Val-Arg-Leu-Gln (described in patent FR 2 879 924) used for their action in the decoupling between coenzyme reoxidation and phosphorylation of ADP into ATP in the mitochondria. Plant extracts, such as marine algae extract of the Palmaria or Rhodymenia genus (described in patent FR 2 887 447), gingko biloba extracts (see patent FR 2 669 537), or soy flavones or isoflavones (described in patent WO 01/64177).

However, these products generally have moderate or limited efficacy over time. It is therefore important to provide new active cosmetic agents having remarkable efficacy as slimming active agents. The inventors have indeed demonstrated that a *Nelumbo nucifera* (Lotus) Extract promotes the release of glycerol from the adipocyte during lipolysis.

The invention and the resulting advantages will be better understood upon reading the description.

The solution to the technical problem addressed lies in the cosmetic use of the association of a *Nelumbo nucifera* (Lotus) Extract. The inventors have indeed demonstrated that a *Nelumbo nucifera* (Lotus) Extract promotes the release of glycerol from the adipocyte during lipolysis.

The invention and the resulting advantages will be better understood upon reading the description.

The foregoing introduction is presented solely to provide a better understanding of the nature of the problems confronting the art and should not be construed in any way as an admission as to prior art nor should the citation of any reference herein be construed as an admission that such reference constitutes "prior art" to the instant application.

SUMMARY

The main aspect of the present invention is directed to a method for increasing lipolysis, slimming and draining using bioactive botanical cosmetic composition obtained from *Nelumbo nucifera* Gaertn. (Lotus) fresh (living) plant. The present invention also relates to the methods for preparing these bioactive botanical cosmetic compositions and the uses of these compositions in various formulations and as topical skin applications.

BRIEF DESCRIPTION OF THE DRAWINGS

Further embodiments of the present invention can be understood with the appended figures.

FIG. 1 is a schematic drawing demonstrating one embodiment of the process for preparing the bioactive botanical agent.

DETAILED DESCRIPTION

Detailed embodiments of the present invention are disclosed herein; however, it is to be understood that the disclosed embodiments are merely illustrative of the invention that may be embodied in various forms. Therefore, specific structural and functional details disclosed herein are not to be interpreted as limiting, but merely as a representative basis for teaching one skilled in the art to variously employ the present invention.

Whenever a term is identified by reference to a range, the range will be understood to explicitly disclose every element thereof. As a non-limiting example, a range of 1-10% will be understood to include 1%, 2%, 3%, 4%, 5%, 6%, 7%, 8%, 9%, and 10%, and all values between 1 and 10%.

Where two or more substituents are referred to as being "selected from" a group of enumerated alternatives, it is meant that each substituent can be any element of that group, independent of the identity of the other substituents.

As used herein, "% refers % by weight, that is the weight percent of a component in relation to the total weight of the composition (i.e., including any carriers, vehicles, solvents, fillers, or other components added before application to the skin) unless otherwise provided.

All terms used herein are intended to have their ordinary meaning unless otherwise provided. For the purposes of describing and claiming the present invention, the following terms are defined:

"Extract" is understood to be any substance or isolated preparation extracted from a natural source, regardless of extraction method or ingredients. The term is used in a broad sense including, for example, ingredients soluble in water or an organic solvent extracted from a natural substance using the solvent, or specific ingredients of a natural substance.

The, "slimming active agent" in the sense of this invention refers to a *Nelumbo nucifera* (Lotus) Extract used to reduce excess localized fat deposit, considered to be unattractive and often associated with a dimpled appearance of the skin.

"Elimination of lipids" refers to the phenomenon of lipolysis leading to the export of glycerol from the adipocyte cell.

"Cellulite" defines a dimpled appearance of the skin, caused by fat cells pushing against the body's connective tissue. The word "cellulite" only refers to how the skin looks, and does not describe a medical condition. Cellulite is associated with the lumps, bumps and dimples that appear on the thighs of many women. Cellulite primarily afflicts the thighs and buttocks but may also be present on the stomach and upper arms. Cellulite is frequently described as "orange peel skin", "mattress phenomena" or the "cottage cheese effect". Cellulite afflictions are a stubborn problem causing emotional and psychological distress to many women.

"Draining" in the sense of invention refers to a better blood and lymphatic microcirculation, a reduction of water retention, a reduction of swelling of the legs, a reduction of the feeling of heavy legs.

This invention first relates to the cosmetic use of a lotus extract (*Nelumbo nucifera*.) as a slimming active agent.

*Nelumbo nucifera* Gaertn. commonly known as Indian lotus or sacred lotus is a species of family Nelumbonaceae. It is native to Tropical Asia and Queensland, Australia, it is commonly cultivated in water gardens. It is also the national flower of India, Bangladesh and Vietnam.

All parts of the lotus such as the fruits, seeds, roots, and leaves are edible and have been used as food for a long time. In addition, these plant parts have been used as antifebrile, sedative, antibacterial, antidiarrheal, and hemostatic agents in folk medicine. Therefore, lotus is widely cultivated and consumed as food and medicine in Korea.

Lotus leaves and petals are used for tea and are commercially available in Korea. Lotus leaves are also consumed as food such as Yeon Yip Bap, which is steamed rice wrapped in lotus leaves. This dish was derived from temple food and has come into wide use due to the various beneficial effects of lotus leaves. Previous studies have revealed the pharmacological effects of lotus leaves, including anti-oxidant, anti-HIV, antidiabetic and anti-obesity. Several bioactive phytocompounds derived from these plant parts were belonging to different chemical groups, including alkaloids, flavonoids, glycosides, triterpenoid, and vitamins (Mukherjee P K et al. "The sacred lotus (*Nelumbo nucifera*): phytochemical and therapeutic profile". Journal of Pharmacy and Pharmacology. 2009; 61(4):407-422.).

Leaves, roots, and the embryonic stage of *N. nucifera* have been reported to contain alkaloids such as roemerine, nuciferine, nornuciferine, nelumboside, anonaine, 5-methoxy-6-hydroxyaporphine, liensinine, and asimilobine ("Rastogi R P, Mehrotra B N. Compendium of Indian Medicinal Plants. Vol. 1. New Delhi, India: Central Drug Research Institute, Lucknow and Publications & Information Directorate; 1991. ((1960-1969), pp. 288-289)"). Bisbenzylisoquinoline alkaloids from *N. nucifera* were shown to be bioavailable after oral administration to rats at a dose of 20 mg/kg (Huang Y, et al. "Simultaneous determination of liensinine, isoliensinine and neferine from seed embryo of *Nelumbo nucifera* Gaertn. in rat plasma by a rapid HPLC method and its application to a pharmacokinetic study". Arzneimittel-Forschung. 2011; 61(6):347-352).

Several flavonoids and nonflavonoids from flowers of *N. nucifera* reported by several authors were consolidated in a review by Mukherjee et al. Flavonoids includemyricetin-3-O-b-D-glucopyranoside, quercetin-3-O-b-D-glucuronide, astragalin, quercetin, 3,4-dihydroxybenzoic, kaempferol, phydroxybenzoic acid, and b-sitosterol which were isolated from ethanol extract of the petals of *N. nucifera* (X. Shuangshuang, et al, "Isolation and characterization of chemical constituents from the petals of *Nelumbo nucifera*," Asian Journal of Chemistry, vol. 24, pp. 4619-4622, 2012). Non-flavonoid compounds, including adenine, myo-inositol, arbutin, and sitosterol glucopyranoside, were identified in flower extract.

The antiobesity effect of a flavonoid-enriched extract from *N. nucifera* leaf (NLFE) in high-fat diet (HFD) fed C57BL/6 mice and its action via lipid-regulated enzymes, thereby attenuating body lipid accumulation and preventing obesity was demonstrated by (Wu et al, "Improvement in high-fat diet-induced obesity and body fat accumulation by a *Nelumbo nucifera* leaf flavonoid-rich extract in mice," Journal of Agricultural and Food Chemistry, vol. 58, no. 11, pp. 7075-7081, 2010). Antiobesity action of leaves and seeds of *N. nucifera* was extensively studied in in vitro and in vivo models by many researchers.

The *Nelumbo nucifera* (Lotus) Extract thereof, used according to the invention, provides in particular the following advantages:
- it promotes lipolysis, the elimination of lipids and the export of glycerol from the adipocytes,
- it smoothes the skin and microrelief of the skin, decreasing "orange peel" aspect,
- it reduces excess of localized fat deposits, modeling and firming the treated skin areas,
- It restores blood flow and limits stasis, improves skin microcirculation, reduces water retention, draining the treated area.

"Topical application" refers to the application or spreading of the active agent according to the invention, or a composition containing it, on the surface of the skin or a mucous membrane.

"Physiologically acceptable" means that the active agent according to the invention, or a composition containing it, is suitable for coming into contact with the skin or a mucous membrane without causing reactions of toxicity or intolerance.

"Physiologically acceptable" refers to any compound adapted to come into contact with the skin or a mucous membrane without causing reactions of toxicity or intolerance.

"Excess localized fat deposit" refers to a hypertrophied area of the subcutaneous adipose tissue, which may have an "orange peel" appearance In the description below, the terms "slimming active agent" and "*Nelumbo nucifera* (Lotus) Extract" will be used interchangeably.

The active agent according to the invention may be obtained by a process described in patent application US2015/0258012.

The present invention relates to a cosmetic care method including the topical application of a botanical fraction of *Nelumbo nucifera* (lotus) extract obtained from fresh plant biomass. Preparation of such botanical fractions were described in patent application US2015/0258012, incorporated herein by reference.

FIG. 1 is a schematic drawing demonstrating one embodiment of the process for preparing the bioactive botanical cosmetic compositions used in the present invention.

Bioactive ingredient from living Lotus plant was obtained according to the Zeta fraction technology process described in U.S. Pat. Nos. 7,442,391; 7,473,435; 7,537,791; 8,043,635; 8,101,212; 8,277,852; 8,318,220; U.S. Pat. Application 20150258012; and PCT/EP2013/073565. This manufacturing process employs grinding and pressing fresh living plants in order to obtain a plant cell juice (intracellular colloidal dispersion), and treat it with an electromagnetic waves at a frequency effective to initiate separation of membrane fraction from cell juice in order to yield a cell cytoplasm/cytosole fraction substantially free from membrane fraction.

The cytoplasm/cytosole fraction is further processed under conditions effective to separate the cytoplasm/cytosole fraction into its component parts, e.g. cytoplasm fraction and a cytosole fraction. The cytosole fraction contains predominantly the low molecular weight components dissolved in the intracellular water. Cytosole fraction is then refined and stabilized to produce the bioactive ingredient, *Nelumbo nucifera* (Lotus) Extract (it is also known as lotus serum fraction, Recentia® NN and Harmoniance™).

The process for the preparation of botanical fractions from fresh plant biomass used in the present invention comprises grinding (or maceration) and pressing fresh plant biomass in order to obtain an intracellular plant material, referred to herein as plant cell juice, containing membrane fractions, and treating said cell juice with an electromagnetic waves at a frequency effective to trigger separation of said membrane fraction from said cell juice fraction in order to yield a cell cytoplasm/cytosole fraction substantially-free from membrane fractions. The aforementioned treatment is advantageously performed such that the temperature of said cell juice during said treatment does not exceed 40° C.

The membrane fraction can then be utilized in order to provide a stable botanical cosmetic composition exhibiting antiproteolytic, cell growth inhibition activity, and/or both antiproteolytic and cell growth inhibition activities, where the antiproteolytic activity is due to inhibition of at least one proteinase and the cell growth inhibition activity is due to inhibition of cell growth of at least one type of cell.

The cytoplasm/cytosole fraction can be utilized in order to provide a botanical composition suitable for use as a component in a pharmaceutical, cosmetic, nutritional, therapeutic and/or personal care formulation and the like.

Overall Process for Preparing Botanical Fractions of the Invention

By way of example, the overall process for preparing the bioactive botanical cosmetic compositions of the present invention is described below in reference to FIG. 1. As depicted in FIG. 1, fresh plants are harvested, collected, and washed to yield fresh plant biomass 2. This fresh plant biomass is subjected to grinding, maceration, and pressing 4 to yield intracellular plant material (cell juice) 6 and fiber-enriched material (press-cake) 8. Cell juice 6 is then filtered through nylon mesh 10 to yield filtered plant cell juice 12. Filtered cell juice 12 is exposed to electromagnetic waves treatment 14 at a frequency to trigger its destabilization. The destabilized cell juice is and then subjected to centrifugation 18 in order to yield precipitated membrane fraction 20 and a supernatant which is cytoplasm/cytosole fraction 30. Membrane fraction 20 is a bioactive botanical cosmetic composition which can be added into cosmetic products as described for example, in U.S. Pat. Nos. 7,442,391, 8,101, 212, 8,277, 852 and 8,318,220. Plant cytoplasm/cytosole fraction 30 is used for further processes, as described below.

Cytoplasm/cytosole fraction 30 can optionally be subjected to additional treatments: i, ii, iii or iv. as summarized below. As a non limiting example, treatment (i) can include isoelectric precipitation 32 and following centrifugation 34 enabling to separate precipitated cytoplasm fraction 36 from supernatant containing cytosole fraction 38, as described for example, in U.S. Pat. Nos. 7,442,391, 8,101,212, and 8,277, 852. Alternatively, cytosole/cytoplasm fraction can be further separated as result of (ii) additional electromagnetic treatment (at frequency >7 GHz) with following centrifugation or filtration, or (iii) membrane filtration, or (iv) ultrafiltration, or combination of thereof (i, ii, iii, iv). Cytoplasm/cytosole fraction components can be utilized "as is" or can be further separated and utilized. They can also be stabilized with preservatives and antioxidants as described for example, in U.S. Pat. Nos. 7,442,391; 7,473,435; 7,537, 791; 8,043,635; 8,101,212; 8,277,852 and 8,318,220.

The plant cell juice may be prepared from all types of plants. Suitable plants that may be used to realize the present invention include, without limitation, plants from the Nelumbonaceae family One preferred embodiment of the present invention uses Lotus (*Nelumbo nucifera*) whole plant.

The plant cell juice may be separated using various separation techniques. However, the separation technique resulting in plant cell juice that preserves the bioactive components of the plant. An exemplary method of preparing the plant biomass for use in extraction of plant cell juice involves harvesting, collecting, and washing of the fresh plants. Suitable steps to follow for preparing the fresh plant biomass include, for example, the following: (1) preservation of the inherent moisture content of the plant cells; (2) preservation of plant integrity during harvesting; (3) minimization of environmental impact and time factors of biological degradation of the plant biomass; and (4) cleaning of the plant biomass prior to processing (e.g., prior to grinding and maceration).

Each of these steps is discussed below.

Preservation of Inherent Moisture Content:

The harvesting of the plants should be done to avoid wilting due to moisture loss. Optimal conditions are those where natural moisture content is maintained and preserved.

One preferred embodiment of the present invention uses Lotus (Nelumbo nucifera) whole plant harvested prior to extraction of the plant cell juice.

Preservation of Plant Integrity During Harvesting:

Harvesting of the plant biomass is conducted in a manner that avoids or minimizes the chopping, mashing, crushing, or other type of injury of the plant. For example, in one embodiment of the present invention, whole plants are collected by hand. One preferred embodiment of the present invention uses Lotus (Nelumbo nucifera) whole plant.

Minimization of Environmental Impact and Time Factors of Degradation:

Delivery time of cut plant material to the processing facility and exposure of biomass to sun, high temperature, and other negative environmental factors, should be minimized to prevent the impact of unwanted degradation processes as described above. In one embodiment, plants that undergo long distance transport are treated to a post-cutting procedure involving immediately placing the plant biomass into Styrofoam coolers containing bags of frozen gel packs to help maintain freshness and natural moisture content during overnight delivery to the processing facility. Other post-harvesting procedures that achieve the results described above may be used as well. As a non-limiting example, for many plant species it is beneficial to not only minimize delivery time for processing, but to also keep the cut plant material cool, by refrigeration if necessary, to prevent and/or minimize unwanted degradation prior to and/or during processing.

Cleaning Step Prior to Grinding and Maceration:

A washing step to remove the soil particles and other debris from plants prior to further processing is performed once the plant tissue is harvested. The washing is achieved using a low-pressure rinse for a short duration under conditions to prevent the initiation of the release of the cell juice from biomass, to cause injury, or to remove valuable components.

For example, in one embodiment of the present invention, the washing of the plant biomass was accomplished in less than or equal to S minutes with a water pressure of less than or equal to 1 kg/cm2. Residual water wash did not contain any green or yellow pigments, which indicates the absence of subsequent injury. The excess water is removed from washed biomass in order to keep the dry matter content close to natural level. After the plant tissue biomass is harvested, as described above, further processing of the plant tissue biomass is performed to yield plant cell juice. In one embodiment, the harvested plant tissue biomass is subjected to grinding, maceration, and pressing to separate the intracellular content, i.e., the cell juice, and to separate it from the fiber-enriched press-cake containing predominantly cell walls.

An example of a suitable processing protocol involves the steps described below. A hammer mill may be used to grind plants to yield plant tissue particles of a small size in a short time and without significant increase of biomass temperature. In one embodiment, a modified hammer mill is used to produce the maximum size of macerated plant particles less than or equal to 0.5 centimeters during less than or equal to 10 seconds of treatment, where the increase of biomass temperature is less than or equal to 5° C.

Exposure of ground and macerated plant biomass is minimized to prevent the impact of unwanted catabolic processes, as described above. The separation of plant cell juice from fiber-enriched material (or press-cake) is commenced as soon as possible after grinding and maceration of the plant biomass. The plant biomass is processed in a short time and without significant increase in temperature. In one embodiment, immediately after grinding and maceration, the plant biomass is pressed using a horizontal, continuous screw press (Compact Press "CP-6", Vincent Corporation, FL). The pressure on the cone is maintained at level 24 $kg/cm^2$, screw speed is at 12 rpm, and biomass temperature increase is less than or equal to 5° C.

The initial cell juice usually contains small fiber particles, which can absorb valuable cell juice components and also block the hoses and pumps. The above particles should be removed by filtration or low-speed centrifugation.

For example, the initial cell juices produced after the pressing step are filtered through four layers of nylon fabric prior to using the plant cell juice in the methods of the present invention.

Once plant cell juice is separated, the plant cell juice is relatively stable colloidal dispersion in which organelles represent the dispersed phase and cytoplasm represents the continuous phase.

Cell juice is then treated to a processes involving (1) triggering destabilization of above colloidal dispersion performing a "initiation of membrane fraction aggregation step" to yield a destabilized cell juice and (2) performing a "membrane fraction separation step" on destabilized cell juice mixture to yield a membrane fraction (containing nucleons, or chloroplasts, or chromoplasts, or mitochondria, or combination of thereof) and a cell juice supernatant. In one embodiment, initiation of membrane fraction destabilization is accomplished by subjecting said cell juice to electromagnetic waves at a frequency of greater than 2.45 GHz. After destabilization is achieved, a membrane fraction separation step is performed. This step includes, for example, separating of destabilized cell juice into the membrane fraction and the cell juice supernatant using separating techniques including filtration, or centrifugation, or combination of thereof.

A variety of instruments can be employed in the process of the invention in order to generate the electromagnetic waves necessary to destabilize the cell juice: magnetrons, power grid tubes, klystrons, klystrodes, crossed-field amplifier, travelling wave tubes, and gyrotrons. One such instrument includes, but is not limited to high power magnetron Conventional and industrial magnetrons operate at a frequency of 915 MHz and 2.45 GHz. However, at those frequencies undesirable heat is generated that can denature the cell juice composition. In the process of the present invention, the electromagnetic waves operate at frequencies that are substantial higher than the frequencies of conventional or industrial magnetrons, which allows for destabilization of the cell juice without undesirable denaturing due to heat generation. The frequency of said electromagnetic waves in the destabilization step of the present invention is above the frequency of conventional microwave magnetrons, i.e., above 2.45 GHz, in another embodiment greater than 2.45 GHz and less than about 7 GHz; and in another embodiment from about 3 to about 6 GHz. During the destabilizing step of the invention the temperature of the cell juice is beneficially maintained below 40° C., in another embodiment below about 25° C., in another embodiment below about 30° C., in another embodiment below about 25° C., in another embodiment below about 20° C.

The freshly obtained membrane fraction commonly referred to in the art, as "protein-vitamin concentrate," is a paste having intensive color and specific odor that is plant raw material source specific. The membrane fraction is represented predominantly by chloroplasts present in the green parts of plant or mostly by chromoplasts present in flowers.

The composition of the membrane fraction includes predominantly phospholipids, membrane proteins, chlorophyll, nucleus, mitochondria and carotenoids. Process for Preparing Cytoplasm/Cytosole Fraction Derived Cosmetic Compositions Substantially-Free from Membrane Fractions.

The method for preparing the cytoplasm/cytosole fraction derived cosmetic compositions substantially-free from membrane fractions exhibiting antioxidant activity, cell growth stimulation activity, or both antioxidant and cell growth stimulation activities involves providing a cell juice that has been separated from a fresh plant biomass, as already described above with respect to the Membrane-Derived Cosmetic Composition. The plant cell juice is then treated under conditions effective to separate the plant cell juice into a membrane fraction and a cytoplasm/cytosole fraction.

The cytoplasm/cytosole fraction can then be optionally further processed under conditions effective to separate the cytoplasm/cytosole fraction into its component parts, namely the cytoplasm fraction and a cytosole fraction. The cytoplasm fraction includes predominantly white soluble proteins; in C3 plants, these proteins largely consist of the enzyme ribulose-5-biphosphate carboxylase oxygenase. The cytosole fraction contains low molecular weight soluble components. Cytosole fraction is refined under conditions effective to yield a cell serum fraction having various biological activities. The cell serum fraction is stabilized under conditions effective to yield a stable bioactive botanical cosmetic composition exhibiting biological activities as described for example, in U.S. Pat. Nos. 7,442,391; 7,473,435; 7,537,791; 8,043,635; 8,101,212; 8,277,852 and 8,318,220.

The plant cell juice may be obtained from all types of plants. Examples of suitable plants that may be used as sources of fresh plant biomass in the present include, without limitation, plants from the Nelumbonaceae family Various parts of the plants may be used. In one preferred embodiment, *Nelumbo nucifera* (Lotus) whole plant is used As described above, once the plant cell juice is separated into membrane fraction and a cell juice supernatant, i.e. cytoplasm/cytosole fraction 30 which is subjected to additional treatments: i, ii, iii or iv (FIG. 1) enabling to separate cytoplasm fraction from cytosole fraction.

The quantitative criteria to evaluate the complete separation of cytoplasm fraction is the absence of detectable levels of high molecular weight proteins and/or the absence of ribulose 1,5-biphosphate carboxilase oxygenase in cytosole fraction.

The cytosole fraction is clear liquid which has a slight yellow color and slight characteristic odor. In several hours, the unstable cytosole fraction is irreversibly transformed into dark brown color suspension containing heavy precipitate and strong non-characteristic odor. As a result, cytosole fraction cannot be used as a cosmetic ingredient. The described procedure that follows allows for the refinement of cytosole fraction to yield stable and active serum fraction which is stable cosmetic ingredients. This is accomplished by removing from cytosole fraction the major components responsible for the irreversible transformations that lead to generation of unwanted precipitate and deterioration of color and odor. This procedure includes: pH adjustment, heat treatment, cooling, vacuum filtration, and stabilization as described in U.S. Pat. Nos. 7,442,391, 8,101,212, 8,277,852 and 8,318,220, which are all incorporated herein by reference.

After the cell serum fraction is produced, it is then subjected to the stabilizing step to yield the Serum-Derived Cosmetic Composition. In one embodiment, the stabilizing step involves incubating the cell serum fraction in a mixture of at least one preservative and at least one antioxidant to yield a stabilized cell serum fraction. Suitable preservatives for use in the present invention include, for example, potassium sorbate, sodium benzoate. An example of a suitable antioxidant for use in the present invention is sodium meta bisulfite.

The present invention relates to a cosmetic care method including the topical application, on at least a portion of the skin of the body or face, of a *Nelumbo nucifera* (Lotus) extract (it is also known as lotus serum fraction, Harmoniance™ and Recentia® NN) in a composition containing a physiologically acceptable medium, in order to obtain a slimming effect, and more specifically in order to reduce excess localized body fat.

The present invention relates to the use of a *Nelumbo nucifera* (Lotus) extract (it is also known as lotus serum fraction, Harmoniance™ and Recentia® NN) in order to promote lipolysis, glycerol release from the adipocytes.

The characteristic biological activity of the invention is defined in vitro by the capacity of the slimming active agent to reduce the size and number of lipid droplets in the adipocytes.

The present invention also relates to a cosmetic care method including the topical application, on at least a portion of the skin of the body or face, of a *Nelumbo nucifera* (lotus) extract in a composition containing a physiologically acceptable medium, in order to obtain a slimming effect, and more specifically in order to reduce excess localized fat deposit.

The present invention relates to a cosmetic method, for slimming, firming and smoothing the skin, in particular in the case of cellulite, the cosmetic composition being applied topically.

Ways and means of slimming, firming and smoothing the skin are an important cosmetic challenge. An undesirable consequence of the formation of fatty tissue in the skin is, in particular, cellulite.

Cellulite is a term for non-inflammatory constitutional (gender-typical) adiposis with mild formation of edema in the connective tissue zone (so-called Adipositas circumscripta oedematosa). Cellulite is found in particular in women in the hip, thigh and gluteal region. In most cases, a so-called "quilt syndrome" (connective tissue septation resulting in reticulate dimpling of the surface) and the so-called "orange-peel skin syndrome" (infundibuliform follicular retractions after squeezing). This results in connective tissue disorder of the subcutis and an increase in the bulk of lipids in the fat cavities. However, cellulite symptoms are not pathological.

By "slimming" or "thinning" or "reducing localized excess weight" means according to the present invention an action to avoid or at least reduce the formation of subcutaneous fat as described above. This action results in particular in a reduction in unsightly excesses or reserves, a refinement of the silhouette by accelerating the removal of excesses, by better defining the contour of the body or a re-sculpted silhouette.

By method of "cosmetic treatment to fight against localized excess weight" and "to improve/promote smooth skin surface" is meant, according to the present invention, the implementation of a cosmetic treatment to measure visibly the action described above.

Thus, a topical composition comprising an efficient amount of a *Nelumbo nucifera* (lotus) extract (also known as lotus serum fraction, Harmoniance™ and Recentia® NN) according to the invention can be applied to the areas of skin liable to form this localized excess weight, namely areas where these overloads are already formed or being formed.

The present invention discloses the uses of a *Nelumbo nucifera* (lotus) extract (also known as lotus serum fraction, Harmoniance™ and Recentia® NN) to reduce excess of localized fat deposits. For the purpose of this invention, unless further limited, the term "reduce" means to diminish the volume, size, mass, bulk, density, amount, and/or quantity of a substance. For example, fat reduction can include reducing fat cell amount (for example, fat cell number), reducing fat cell volume, reducing fat cell maturation, and/or dedifferentiating of fat cell.

Specifically, the invention envisions new uses for the *Nelumbo nucifera* (lotus) extract (also known as lotus serum fraction, Harmoniance™ and Recentia® NN) when administered topically to the skin, especially in the area of excess of fat deposits, of an individual, for example, a mammal, for example, a human.

The invention is further expected to be useful for individuals with prominent or undesired deposits of fat on the abdomen, chest, buttocks, hips, thighs, legs, knees, arms, chin, face, or neck.

The invention is also conceived to be beneficial for individuals affected with pathologies such as obesity Cushing syndrome, pseudo-Cushing syndrome, drug-induced obesity, HIV-related lipodystrophy, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, or leptin deficiency or resistance. The invention is further contemplated to be of utility for individuals using cortisol and analogs, other corticosteroids, megace, sulfonylureas, trycyclic antidepressants, monoamine oxidase inhibitors, selective serotonin reuptake inhibitors, oral contraceptives, insulin, risperidone, clozapine, and thiazolidinediones.

Advantageously, the *Nelumbo nucifera* (lotus) extract according to the invention is present in a concentration adapted to be physiologically acceptable for a topical use.

*Nelumbo nucifera* (Lotus) Extract according to the invention was tested at the concentrations up to 100% (non-diluted) and was found not irritant, very well tolerated in human, and in addition, it demonstrated no phototoxic potential in phototoxicity in vitro study. Advantageously, the *Nelumbo nucifera* (Lotus) Extract is present in a concentration ranging between 0.001% and 10%, preferably between 0.1 and 2.5% and more preferably between 0.2 and 1% of the total weight of the composition, in a physiologically acceptable medium.

The compositions for implementation of the invention may in particular be in the form of an aqueous, hydroalcoholic or oily solution; and oil-in-water emulsion, a water-in-oil emulsion or multiple emulsions; they may also be in the form of suspensions, or powders, suitable for application on the skin, mucous membranes, lips and/or hair.

These compositions may be more or less fluid and have the appearance of a cream, a lotion, a milk, a serum, a pomade, a gel, a paste or a foam. They may also be in solid form such as a stick or be applied on the skin in the form of aerosol.

These compositions may also include any additive commonly used in the field of application envisaged, as well as the adjuvants necessary for their formulation, such as solvents, thickeners, diluents, antioxidants, coloring agents, sunscreens, self-tanning agents, pigments, fillers, preservatives, fragrances, odor absorbers, cosmetic or pharmaceutical active agents, essential oils, vitamins, essential fatty acids, surfactants, film-forming polymers, and so on.

In every case, a person skilled in the art will ensure that said adjuvants as well as the proportions thereof are chosen so as not to interfere with the desired advantageous properties of the composition of the invention. These adjuvants may, for example, correspond to 0.01 to 20% of the total weight of the composition. When the composition of the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field considered. For example, they may be used in a proportion ranging from 0.3 to 30% by weight, with respect to the total weight of the composition.

Advantageously, the composition capable of being used for the invention may include, in addition to the slimming active agent according to the invention, at least one other active agent having cosmetic effects that are similar and/or complementary to those of the invention. According to the invention, this active agent will be defined as an "additional active agent".

For example, the additional active agent(s) may be chosen from: anti-aging, toning, lightening, hydrating, draining, and microcirculation-promoting agents, pharmaceutical, exfoliating, scrubbing, extracellular matrix-stimulating, energy metabolism-activating, antibacterial, antifungal, calming, anti-free radical, anti-UV and anti-acne agents, anti-inflammatory agents, anesthetics, warming agents, cooling agents and weight-loss agents.

Such additional agents may be chosen from the groups including:

vitamin A and in particular retinoic acid, retinol, retinol propionate, retinol palmitate, vitamin B3 and more specifically niacinamide, tocopherol nicotinate, vitamin B5, vitamin B6, vitamin B12, vitamin C, in particular ascorbic acid, ascorbyl glucoside, ascorbyl tetrapalmitate, magnesium and sodium ascorbyl phosphate, vitamins E, F, H, K, PP, coenzyme Q10 metalloproteinase inhibitors, a TIMP activator

DHEA, precursors and derivatives thereof, amino acids such as arginine, ornithine, hydroxypropline, hydroxyproline dipalmate, palmitoylglycine, hydroxylysine, methionine and derivatives thereof, N-acyl amino acid compounds, natural or synthetic peptides, including di-, tri-, tetra-, penta- and hexapeptides and the lipophilic derivatives thereof, isomers and complexed with other species such as a metal ion (e.g. copper, zinc, manganese, magnesium, and others). For example, the peptides commercially known under the names MATRIXYL™, ARGIRELINE™, COLLAXYL™ PEPTIDE VINCI 02™, CHRONOGEN™, LAMINIXYL IS™, PEPTIDE Q10™, plant-based peptide extracts such as extracts of soy, spelt, grapevine, rapeseed, linseed, rice, corn, pea, yeast extracts, Artemia Salina extracts, dehydroacetic acid (DHA), phytosterols of synthetic or natural origin, salicylic acid and derivatives thereof, alpha- and beta-hydroxyacids, amino sugars, glucosamine, D-glucosamine, N-acetyl-glucosamine, N-acetyl-D-glycosamine, mannosamine, N-acetyl mannosamine, galactosamine, N-acetyl galactosamine extracts of polyphenols, isoflavones, flavonoids, such as grape extracts, pine extracts and olive extracts, lipids such as ceramides or phospholipids, oils of animal origin, such as squalene or squalane; plant oils, such as sweet almond, copra, ricin, jojoba, olive, rapeseed, peanut, sunflower, wheat germ, corn germ, soy, cottonseed, alfalfa, poppy, winter squash, evening primrose, millet, barley, rye, safflower, passion fruit, hazelnut, palm, apricot seed, avocado, and calendula oil; ethoxylated plant oils, and shea butter, all UV screens and sunscreens.

Especially advantageously, the invention may include at least one additional active agent known for its slimming effect action, inhibiting lipogenesis or stimulating lipolysis, such as: cyclic AMP and derivatives thereof, adenylate cyclase enzyme activating agents and phosphodiesterase enzyme inhibiting agents, centalla asiatica extract, asiaticoside and asiatic acid, methyl xanthines, thein, theophylline, theobromine, forskoline, esculin and esculoside, ACE inhibitors, the peptide Val-Trp, neuropeptide Y inhibitors, enkephalin, gingko biloba extract, dioscorea extract, rutin, verba mate extract, guarana extract, oligosaccharides, polysaccharides, carnitine, ivy extract, rockweed extract, hydrolyzed Prunella vulgaris extract, hydrolyzed Celosia cristata extract, Anogeissus leiocarpus extract, Manihot utilissima leaf extract, palmitoylcarnitine, carnosine, taurine, elderberry extract, algae extracts such as *Palmaria Palmata* extract, the synthetic peptide of sequence Arg-Gly-Ser-NH$_2$, sold under the name ATPEPTIDE™, the synthetic peptide of sequence Pro-Leu-Asp-Thr-Ala-Lys-Val-Arg-Leu-Gln sold under the name UCPEPTIDE™.

The composition capable of being used according to the invention may be applied by any suitable route, in particular oral or external topical, and the formulation of the compositions will be adapted by a person skilled in the art.

Advantageously, the compositions according to the invention are in a form suitable for topical application. These compositions must therefore contain a physiologically acceptable medium, i.e. compatible with the skin and skin appendages, and cover all cosmetic forms.

It is obvious that the invention concerns mammals in general, and more specifically human beings.

Specific embodiments of this cosmetic treatment method also result from the above description. Other advantages and features of the invention will be more apparent upon reading the examples provided for illustrative and non-limiting purposes.

Example 1: Analysis of a Bioactive Lotus Serum Fraction (Cytoplasm/Cytosol Fraction or Cell Serum Fraction)

Bioactive ingredient from living Lotus plant was obtained according to the Zeta fraction technology process described in U.S. Pat. Nos. 7,442,391; 7,473,435; 7,537,791; 8,043,635; 8,101,212; 8,277,852; 8,318,220; U.S. Pat. Application 20150258012; and PCT/EP2013/073565. This manufacturing process employs grinding and pressing fresh living plants in order to obtain a plant cell juice (intracellular colloidal dispersion), and treat it with an electromagnetic waves at a frequency effective to initiate separation of membrane fraction from cell juice in order to yield a cell cytoplasm/cytosole fraction substantially free from membrane fraction.

The cytoplasm/cytosole fraction is further processed under conditions effective to separate the cytoplasm/cytosole fraction into its component parts, e.g. cytoplasm fraction and a cytosole fraction. The cytosole fraction contains predominantly the low molecular weight components dissolved in the intracellular water. Cytosole fraction is then refined and stabilized to produce the bioactive ingredient, *Nelumbo nucifera* (Lotus) Extract (it is also known as lotus serum fraction, Recentia® NN and Harmoniance™).

Total soluble sugars analyses in *Nelumbo nucifera* (Lotus) Extract was based on colorimetry method described in: "Estimation of Carbohydrates in Plant Extracts" by Anthrone by Yemm and Willis, Biochem J.; 57(3): 508-514 (1954). The samples analyses were conducted with the following approach: a standard (two-sugar mixture) was made from a combination of ~200 ppm each of fructose and glucose, totaling 414 ppm of monosaccharide. Serial dilutions of this stock standard with water were made and 1 mL of each solution was reacted with 5 mL of ice cold 2000 ppm anthrone in 72% sulfuric acid. The reagents were heated to 100° C. for 10 minutes and a four-point calibration curve was created from the absorbance values of these solutions at 680 nm. Test sample was diluted in water to a 0.5% solution based on weight and the same reaction carried out. The absorbance of these solutions at 680 nm compared against the calibration curve was used to determine their total sugar concentrations. For samples and standards, a quartz 1 cm cuvette was used and a blank absorbance value was taken with pure water.

Total phenolic compound content in *Nelumbo nucifera* (Lotus) Extract was determined by the method described in: "Estimation of total phenolic content and other oxidation substrates in plant tissues using Folin-Ciocalteu reagent" by Ainsworth and Gillespie, Nature Protocols; 2: 875-877 (2007). Colorimetric total phenolics assay described in this paper utilizes Folin-Ciocalteu (F-C) reagent. The F-C assay relies on the transfer of electrons in alkaline medium from phenolic compounds to phosphomolybdic/phosphotungstic acid complexes, which are determined spectroscopically at 765 nm. The samples analyses were conducted according to this method—starting with step 5. The volumes in steps 5, 6 and 7 were doubled to yield sufficient volume for a disposable reduced volume cuvette. Each sample for measurement was prepared in an individual cuvette. In step 6, F-C reagent addition, the sample and reagent were mixed and allowed to stand for ~10 minutes before carbonate addition. At the end of two hours, the samples and standard (chlorogenic acid) solutions were measured at 765 nm versus air; total phenolic content in the samples was calculated using chlorogenic acid (standard) calibration curve.

Safety and toxicologic profile of *Nelumbo nucifera* (Lotus) was assessed using well described methods

*Nelumbo nucifera* (Lotus) Extract was tested at the concentrations up to 100% (non-diluted).

It was found that it is:
Not irritant (demonstrated in skin Irritation studies: reconstructed human epidermis)
Very well tolerated (in human 48 hrs patch test on 10 volunteers):
Practically not irritant (Eye Irritation studies Het-Cam test)
Not irritant (Reconstituted Human Corneal Epithelial (RHCE) Long exposure-time treatment test)

In addition, it demonstrated no phototoxic potential in phototoxicity study (Neutral Red Uptake phototoxicity Test on 3T3 cells, 3T3 NRUPT in vitro method)

TABLE 1

Analytical data and ranges* are presented in Table below.

| | | |
|---|---|---|
| Dry matter (plant based non- volatile solids) | 6.59-6.78 (%) w/w | |
| Total soluble sugars | 2.29-2.54 (%) w/w | ~33.8-38.5% of plant based non-volatile solids (extractives) |

TABLE 1-continued

Analytical data and ranges* are presented in Table below.

| | | |
|---|---|---|
| Total phenolic compounds | 1.33-1.58 (%) w/w | ~19.6-23.9% of plant based non-volatile solids (extractives) |

*Nelumbo nucifera (Lotus) Extract was analyzed "as is".

It is plausible that both groups of compounds do contribute to the biological activities of *Nelumbo nucifera* (Lotus) Extract.

Example 2: Evaluation of *Nelumbo nucifera* (Lotus) Extract on Lipolysis

This study aims to evaluate in vitro effect of *Nelumbo nucifera* (Lotus) Extract on lipolysis by evaluating glycerol release on preadipocytes. Lipolysis is the hydrolysis of triglycerides into glycerol and fatty acids. The amount of glycerol release will be proportional to both the amount of stored triglyceride and the degree of lipolysis Protocol:

3T3-L1 pre-adipocytes (ATCC) were cultured in DMEM 4.5 g/L glucose (Lonza) supplemented with 10% of FBS (Lonza), 2 mM of L-Glutamine (Lonza) and 100 µg/ml of Primocin (InvivoGen).

2 days after the cells' confluence, differentiation into adipocytes was induced by adding 0.5 mM IBMX, 1 µM dexamethasone and 10 µg/ml insulin (Sigma) in the culture medium for 3 days. Afterwards, IBMX and dexamethasone were removed and only the insulin was maintained for 3 to 4 days; then, the insulin was also removed, and the cells were maintained in culture medium for another 3 days.

After differentiation, cells were treated with *Nelumbo nucifera* (Lotus) Extract of example 1 diluted at 1/10.000 eme in culture medium, further noted as Lotus 0.01% (volume/volume) or with 2 mM caffeine positive control, twice a day for 48 hours. Then glycerol release was measured using Adipolysis Assay Kit (Cayman Chemical), according to the manufacturer's instructions.

Results:

The results in table 1 show a significant increase of glycerol release after treatment with *Nelumbo nucifera* (Lotus) Extract compared to untreated condition or compared to the caffeine positive control condition.

TABLE 2

Glycerol release after treatment with *Nelumbo nucifera* (Lotus) Extract

| | Glycerol release (% of untreated) |
|---|---|
| Untreated | 100 |
| Caffeine 2 mM | 131 |
| Lotus 0.01% | 173 |

Conclusion:

*Nelumbo nucifera* (Lotus) Extract at 0.01% stimulates in vitro lipolysis in adipocytes.

Example 3: In Vivo Study of *Nelumbo nucifera* (Lotus) Extract on Slimming Effect Protocol:

20 healthy women volunteers, aged 23 to 48, participated in this comparative double blind study. Volunteers applied the cream formula #TCAAG06 comprising with 0.5% of *Nelumbo nucifera* (Lotus) Extract of example 1 on one thigh and a placebo on the other, twice a day (morning and evening), for 8 weeks. The result of the *Nelumbo nucifera* (Lotus) Extract effect was determined by centimeter measurements of the up and down part of the thigh (circumference), temperature evaluation of the up part of the thigh and trained expert and volunteer visual assessment. Student's t-test (one-tailed) or Wilcoxon signed rank test (one-tailed) are used depending on whether the data followed a normal distribution or not. The control visite have been done at D0, D28 and D56. Concerning the statistical analysis, Student's t-test (one-tailed) or Wilcoxon signed rank test (one-tailed) are used depending on whether the data followed a normal distribution or not.

Results:

Centimeter Measurement: Concerning the Centimeter Measurement of the Up Part of the Thigh we observed a significant decrease of the thigh circumference after 2 months of application.

TABLE 3

| Treated sides | Time | Mean (cm) | sem | p | % of change | % of improved volunteers |
|---|---|---|---|---|---|---|
| Placebo | D28-D0 | 0.033 | 0.081 | $0.4918^{ns}$ | −0.01% | 45% (9/20) |
| 0.5% *Nelumbo nucifera* (Lotus) Extract | | 0.03 | 0.118 | | | |
| Placebo | D56-D0 | −0.04 | 0.109 | 0.0056** | −0.88% | 75% (15/20) |
| 0.5% *Nelumbo nucifera* (Lotus) Extract | | −0.55 | 0.14 | | | |

On the down part of the thigh we noticed a very significant decrease of the circumference after one month of application. This decrease kept improving after 2 months of application.

TABLE 4

| Treated sides | Time | Mean (cm) | sem | p | % of change (new) | % of improved volunteers |
|---|---|---|---|---|---|---|
| Placebo | D28-D0 | −0.25 | 0.122 | 0.0079** | −1.06% | 65% (13/20) |
| 0.5% *Nelumbo nucifera* (Lotus) Extract | | −0.69 | 0.138 | | | |

TABLE 4-continued

| Treated sides | Time | Mean (cm) | sem | p | % of change (new) | % of improved volunteers |
|---|---|---|---|---|---|---|
| Placebo | D56-D0 | −0.41 | 0.128 | 0.0012*** | −1.83% | 90% (18/20) |
| 0.5% Nelumbo nucifera (Lotus) Extract | | −1.18 | 0.187 | | | |

Temperature Measurement:

Cellulite is due to the triglyceride storage in adiposities leading to nodular that induce compression of blood vessels and lymphatic tissue congestion. This compression causes a slowing of blood flow and water retention, it follows a heterogeneity of the skin temperature.

To observed the heterogeneity of skin temperature, measures have been done every centimeter on a length of 20 cm on the up part of the thigh. Then, the difference between the temperature minimal and the temperature maximal was compared for each volunteer, in order to observed the temperature amplitude for both treated zones.

Thanks to 2 months of application with 0.5% Nelumbo nucifera (Lotus) Extract, we noticed a significant decrease in the skin temperature amplitude highlighted a better homogeneity of the skin temperature compared to the placebo sides. These results indicated that Nelumbo nucifera (Lotus) Extract at 0.5% may help restored blood flow and limited water retention.

TABLE 5

| Treated sides | Time | Mean | sem | p | % of change | % of improved volunteers |
|---|---|---|---|---|---|---|
| Placebo | D28-D0 | 0.59 | 0.098 | 0.1527$^{ns}$ | −6.67% | 55% (11/20) |
| 0.5% Nelumbo nucifera (Lotus) Extract | | 0.47 | 0.069 | | | |
| Placebo | D56-D0 | 0.58 | 0.109 | 0.0187* | −14.72% | 65% (13/20) |
| 0.5% Nelumbo nucifera (Lotus) Extract | | 0.315 | 0.068 | | | |

Trained Expert and Volunteer Assessment:

At D56, on 60% of the volunteers, the trained expert found the thigh treated with 0.5% Nelumbo nucifera (Lotus) Extract containing cream, thinner and more pleasant to the touch.

60% of the volunteers found the thigh treated with 0.5% Nelumbo nucifera (Lotus) Extract containing cream thinner and 55% found that skin touch was more enjoyable after 2 months of 0.5% Nelumbo nucifera (Lotus) Extract applications.

Conclusion:

One month after creams application we noticed that Nelumbo nucifera (Lotus) Extract formulated at 0.5% significantly decrease the circumference of the down part of the thigh compared to placebo. This improvement was confirmed after two months of application by the significant decrease of the thigh circumference on the both areas of measurement.

We also noticed after 2 months of application with 0.5% Nelumbo nucifera (Lotus) Extract a significant improvement of the homogeneity of the skin temperature demonstrated that Nelumbo nucifera (Lotus) Extract may help restored blood flow and limited stasis Moreover, the majority of the volunteers found the thigh treated with 0.5% Nelumbo nucifera (Lotus) Extract thinner and more pleasant to the touch following the 2 months of treatment. All these parameters highlighted the potential of Nelumbo nucifera (Lotus) Extract to promote slimming and draining by its beneficial effect on thigh circumference and on the homogeneity of the skin temperature.

Example 4: Clinical Test Cream—Lotus #TCAAG06

| Ingredients (Trade Name | INCI) | | % w/w | Supplier |
|---|---|---|---|
| Phase A | | | |
| Purified Water | Water/Aqua | Qs. 100 | |
| EDTA tetrasodium Salt | Tetrasodium EDTA | 0.05 | Fisher |

-continued

| Ingredients (Trade Name | INCI) | % w/w | Supplier |
|---|---|---|---|
| Lubrajel* MS Free hydrogel | Water/Aqua (and) Glycerin (and) Glyceryl Acrylate/Acrylic Acid Copolymer (and) Phenoxyethanol | 3.00 | Ashland |
| LiquaPar ™/Rokonsal ™ MEP preservative | Phenoxyethanol (and) Methylparaben (and) Ethylparaben (and) Propylparaben | 1.00 | Ashland |
| UltraThix ™ P-100 polymer | Acrylic Acid/VP Crosspolymer | 0.60 | Ashland |
| Sodium Hydroxide | Sodium Hydroxide | 0.02 | Fisher |
| Purified Water | Water/Aqua | 0.50 | / |
| Belsil ™ W3230* | Bis-Stearoxydimethylsilane (and) stearyl alcohol (and) Dimethicone | 2.00 | Wacker |
| Simulsol ™ 165* | PEG-100 Stearate (and) Glyceryl Stearate | 2.00 | Seppic |
| Refined Shea Butter | *Butyrospermum Parkii* (Shea) Butter | 2.00 | Ashland |
| Ceraphyl ™ 28 ester | Cetyl Lactate | 1.50 | Ashland |
| Ceraphyl ™ 791 ester | Isocetyl Stearoyl Stearate | 2.00 | Ashland |
| Ceraphyl ™ ODS ester | Octyldodecyl Stearate | 3.00 | Ashland |
| Ceraphyl ™ 368 ester | Ethylhexyl Palmitate | 4.00 | Ashland |
| Sodium Hydroxide | Sodium Hydroxide | 0.03 | Fisher |
| Purified Water | Water/Aqua | 0.50 | / |
| *Nelumbo nucifera* (Lotus) of example 1 | | 0.50 | Ashland |

Procedure
1. Add phase A into main vessel and begin homogenization. Heat at 70-75° C.
2. Sprinkle in UltraThix P-100 and mix well for approximately 30 min.
3. Add phase D ingredients to side beaker and heat at 70-75° C.
4. Add phase C pre-mixed into phase A until homogeneous
5. At 70-75° C. add phase D into the main vessel and mix well. The emulsion should be homogeneous.
6. Begin cooling.
7. At ~50° C. add phase E pre-mixed and mix well.
8. Below 30° C. add phase F and mix well
9. Stop at 25° C.
Typical Properties
Appearance: White cream
pH: 5.20-5.80
Viscosity (D0) 23000-40000 (Brookfield RVT/Spindle B/5 RPM/1 minute/25° C.)

This formula has passed 3-month accelerated lab stabilities and a 28-day challenge efficacy test. However, the preservative system has not been optimized to its lowest effective level.

The invention claimed is:

1. A cosmetic method for promoting lipolysis, slimming, draining, smoothing skin surface, reducing localized fat deposits, the method comprising applying to an area to be treated a topical composition consisting essentially of:
  i. 0.2 to 1% w/w of Nelumbo nucifera (Lotus) Extract obtained from the whole plant and having a dry matter ranging from between 6.59-6.78% w/w, a total soluble sugars ranging from between 2.29-2.54% w/w and a total phenolic compounds ranging from 1.33-1.58% w/w: and
  ii. a dermatologically acceptable carrier.

2. The cosmetic method of claim 1, wherein the area to be treated is selected from the group consisting of face, chin, neck, arms, chest, abdomen, buttocks, hips, thighs, and legs.

3. The cosmetic method according to claim 1, wherein topically applying comprises application twice a day of the composition that reduces localized fat deposits.

4. The cosmetic method of claim 1, wherein topically applying twice a day consists of applying morning and evening the composition.

* * * * *